United States Patent
Hsu

(10) Patent No.: US 10,946,381 B2
(45) Date of Patent: Mar. 16, 2021

(54) MICROFLUIDIC HYDRODYNAMIC SHUTTLING CHIP DEVICE FOR HIGHTHROUGHPUT MULTIPLE SINGLE CELLS CAPTURE

(71) Applicant: National Health Research Institutes, Zhunan (TW)

(72) Inventor: Chia-Hsien Hsu, Zhunan (TW)

(73) Assignee: NATIONAL HEALTH RESEARCH INSTITUTES, Miaoli County (TW)

( * ) Notice: Subject to any disclaimer, the term of this patent is extended or adjusted under 35 U.S.C. 154(b) by 164 days.

(21) Appl. No.: 15/753,907

(22) PCT Filed: Aug. 13, 2016

(86) PCT No.: PCT/US2016/046944
§ 371 (c)(1),
(2) Date: Feb. 20, 2018

(87) PCT Pub. No.: WO2017/031017
PCT Pub. Date: Feb. 23, 2017

(65) Prior Publication Data
US 2018/0243742 A1 Aug. 30, 2018

Related U.S. Application Data

(60) Provisional application No. 62/206,775, filed on Aug. 18, 2015.

(51) Int. Cl.
*B01L 3/00* (2006.01)
*C12M 1/00* (2006.01)
*C12M 3/06* (2006.01)

(52) U.S. Cl.
CPC ... *B01L 3/502761* (2013.01); *B01L 3/502715* (2013.01); *C12M 23/16* (2013.01); *C12M 47/04* (2013.01); *B01L 2200/0668* (2013.01); *B01L 2300/0816* (2013.01); *B01L 2300/0864* (2013.01); *B01L 2300/0883* (2013.01); *B01L 2300/12* (2013.01); *B01L 2300/16* (2013.01); *B01L 2400/0463* (2013.01); *B01L 2400/0487* (2013.01)

(58) Field of Classification Search
CPC . C12M 23/16; C12M 47/04; B01L 3/502761; B01L 3/502715; B01L 2200/0668; B01L 2300/0816; B01L 2300/0883; B01L 2300/0864; B01L 2300/12; B01L 2300/16; B01L 2400/0463; B01L 2400/0487
See application file for complete search history.

(56) References Cited

U.S. PATENT DOCUMENTS

| | | |
|---|---|---|
| 2009/0053799 A1 | 2/2009 | Chang-Yen et al. |
| 2010/0003666 A1 | 1/2010 | Lee et al. |
| 2012/0318719 A1 | 12/2012 | Lean et al. |
| 2014/0248621 A1 | 9/2014 | Collins |
| 2015/0018226 A1 | 1/2015 | Hansen et al. |

*Primary Examiner* — Teresa E Knight
(74) *Attorney, Agent, or Firm* — Muncy, Geissler, Olds & Lowe, PC

(57) ABSTRACT

A hydrodynamic shuttling chip device comprising an array of single-cell trapping units is disclosed. Each unit comprises: (a) an incoming channel with a cell capture site; (b) a cell culture chamber located posterior to the cell capture site, having a receiving site spaced apart from the cell capture site at a distance of g; (c) a trapping channel located between the cell capture site and the receiving site; (d) a chamber channel located posterior to and in fluidic connection with the cell culture chamber; and (e) a by-pass channel, located lateral to the incoming channel, chamber and chamber channel and having a first end and a second end opposite to the first end, the first end branching out from the incoming channel immediately prior to the cell capture site and the second end joining the chamber channel. A method of capturing single cells of more than one type is also disclosed.

15 Claims, 8 Drawing Sheets

Design 1

FIG. 1E  Design 2
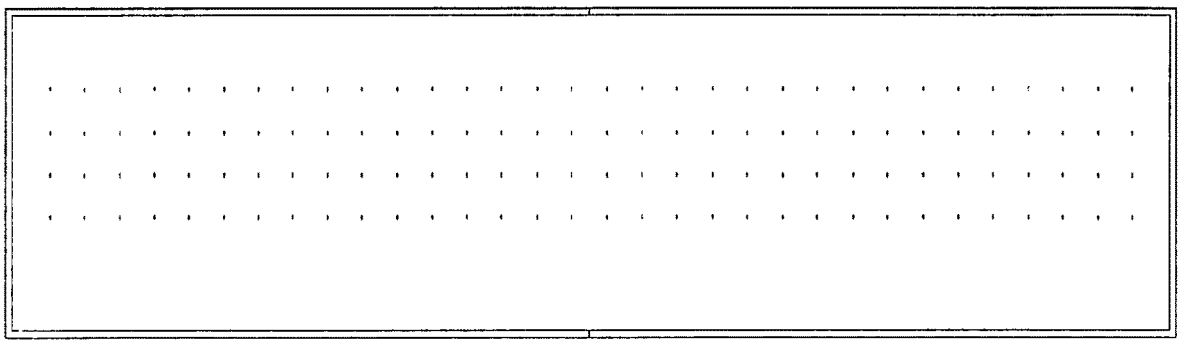
FIG. 1F
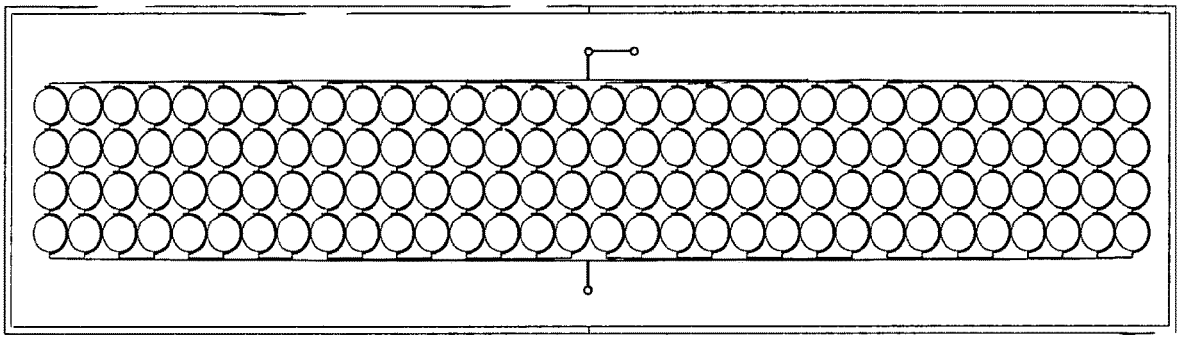
FIG. 1G
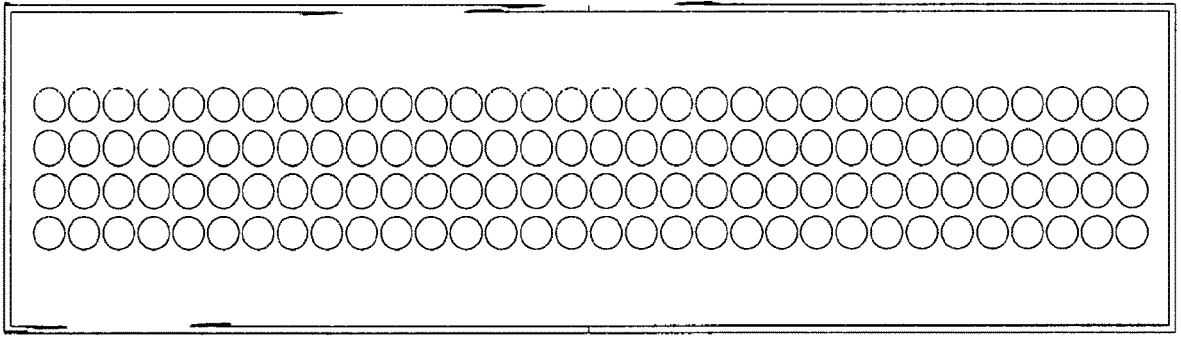
FIG. 1H
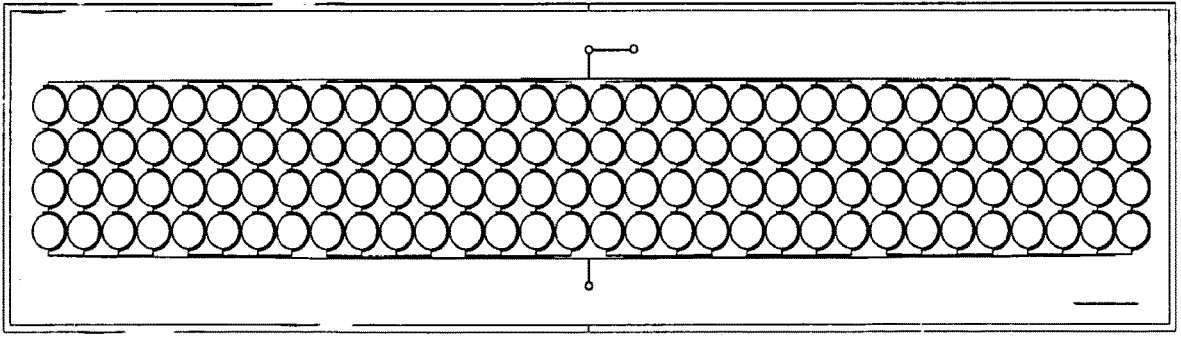

0: empty well
1A: one single MDA-MB-231 cell
1B: one single MCF-7 cel
1A+1B: one single MDA-MB-231 cell and one single MCF-7 cell
>1A+1B: more than one single MDA-MB-231 cell and one single MCF-7 cell

MICROFLUIDIC HYDRODYNAMIC SHUTTLING CHIP DEVICE FOR HIGHTHROUGHPUT MULTIPLE SINGLE CELLS CAPTURE

FIELD OF THE INVENTION

The present invention relates generally to a biological microfluidic chip and more specifically to a hydrodynamic shuttling chip device for trapping and culturing multiple single cells.

BACKGROUND OF THE INVENTION

Microfabricated devices have been recently designed for single cell trapping, single cell pairing and long-term culture, based on their ability to accurately manipulate single cells. They are advantageous because they are high-throughput, low-cost and can reduce reagent consumption. Yamaguchi et al. (*Sens Actuators B Chem.* 2009. 136(2): 555-61) has report a simple device with 30 μm height and 100 μm width channel to enable single cell trapping and culture. The capture efficiency of this device 73%. However this device only allowed the captured cells to grow for up to 24 hours due to its a limited space. Lee et al. (*Integr Biol* (Camb). 2012. 4(4):374-80) used a similar concept to design a single cell co-culture platform for cell-cell interaction studies. The single cell pairing efficiency of this concept device was 50%, but it still lacked a sufficient space for cells to spread and proliferation.

SUMMARY OF THE INVENTION

In one aspect, the invention relates to a hydrodynamic shuttling chip device comprising an array of single-cell trapping units, in which each of the single-cell trapping units comprises:
   (a) an incoming channel with length L1, width W1, and height H1, having an anterior end and a posterior end opposite to the anterior end, wherein the posterior end has a capture site;
   (b) a chamber with diameter M and depth D, located posterior to the capture site of the incoming channel and having a receiving site spaced apart from the capture site at a distance of g, the chamber having an interior space adapted for more than one single cell to attach, grow, proliferate, and/or migrate;
   (c) a trapping channel with length L2, width W2, height H2, located between the capture site and the receiving site and being in fluid connection with the incoming channel and the chamber;
   (d) a chamber channel with length L3, width W3, height H3, located posterior to and in fluidic connection with the chamber and having an anterior end and a posterior end opposite to the anterior end, the height H3 of the chamber channel being smaller than the depth D of the chamber; and
   (e) a by-pass channel with length L4, width W4, and height H4, located lateral to the incoming channel, chamber and chamber channel and having a first end and a second end opposite to the first end, the first end branching out from the incoming channel immediately prior to the capture site and the second end joining the chamber channel at the posterior end thereof, the width W4 and height H4 of the by-pass channel being greater than the width W2 and height H2 of the trapping channel;

wherein in each column of the array:
   (i) The single-cell trapping units are in fluidic connection;
   (ii) The incoming channel of each unit, except the first unit, is in fluid connection with the chamber channel of an immediately upstream unit; and
   (iii) The by-pass channel of each unit, except the last unit, is in fluid connection with the incoming channel of an immediately downstream unit.

In one embodiment, in each column of the array the chamber channel of each unit except the last unit is in fluidic connection with the incoming channel of an immediately adjacent downstream unit.

In another embodiment, in each column of the array the chamber channel of the last unit is in fluid connection with an outgoing channel.

In another embodiment, in each column of the array the incoming channel of the first unit is in fluidic connection with an inlet channel, and the outgoing channel of the last unit is in fluidic connection with an outlet channel.

In another embodiment, the device further comprises: (a) an inlet port, being in fluid connection with the inlet channel; and (b) an outlet port, being in fluidic connection with the outlet channel.

In another embodiment, the single-cell trapping units between columns of the array are in fluidic connection via the inlet channel and outlet channel.

The surfaces of the incoming channel, trapping channel, chamber channel, and by-pass channel may be coated or non-coated.

In one embodiment, the surfaces of the incoming channel, trapping channel, chamber channel, and by-pass channel are coated with albumin, e.g., bovine serum albumin. Other types of surface coating may be used depending on the application of the device.

In another embodiment, the chamber comprises one isolated single cell.

In another embodiment, the chamber comprises two isolated single cells of different types.

In another embodiment, the chamber comprises multiple isolated single cells of different types.

In another embodiment, the chamber comprises multiple isolated single cells of the same type.

In another embodiment, the device comprises one or more than one type of isolated single cells in the chamber.

In another embodiment, the device comprises 2 or more types of isolated single cells in the chamber.

In another embodiment, the device further comprises a single cell suspension, wherein the size of the single cell is smaller than the cross section of the by-pass channel but larger than the cross section of the trapping channel.

In another embodiment, the device is bounded onto a transparent substrate. The substrate may be a pieces of glass.

In another embodiment, the device is made of a material selected from the group consisting of polydimethylsiloxane, polymethyl methacrylate, and polycarbonate, glass, plastic, and any combination thereof.

In another embodiment, the by-pass channel serpentines laterally through one side of the unit.

In another aspect, the invention relates to a method of capturing isolated single cells. The method comprises:
   (a) providing a hydrodynamic shuttling chip device of the invention;
   (b) loading culture medium comprising isolated cells of a single type into the incoming channel of the first single-cell trapping unit in a single row of the array;
   (c) capturing the isolated cells of the single type at the captured sites;

(d) washing away uncaptured, excess cells with a fresh culture medium; and (e) refluxing the channels with a medium to release the captured isolated cells of the single type and reversely flow the released cells into the chambers.

In another aspect, the invention relates to a method of capturing isolated single cells of more than one type, in which the method comprises:

(a) providing a hydrodynamic shuttling chip device of the invention;

(b) loading culture medium comprising isolated single cells of a specific type into the incoming channel of the first single-cell trapping unit in a single row of the array;

(c) capturing the isolated single cells of the specific type at the captured sites;

(d) washing away uncaptured, excess cells with fresh culture medium; and (e) refluxing the chamber channels to release the captured single cells of the specific type and reversely flow the released cells of the specific type into the chambers; and (f) repeating the loading, capturing, washing, and refluxing steps one or more times with the proviso that in each repeating step the isolated single cells are a different type.

In another embodiment, the capturing step captures one isolated single cell per capture site.

In another embodiment, the volumetric flow rate in the refluxing step is greater than that in the washing steps.

In another embodiment, the volumetric flow rate in the refluxing step is no less than the cell-loading step.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIGS. 1A-H are schematic drawings showing the patterns of the mask designs of HSC chips. FIGS. 1A & 1E show top views of the first layer (layer 1) photomask in Designs 1 and 2, respectively. FIGS. 1B & 1F show top views of the second layer (layer 2) photomask in Designs 1 and 2, respectively. FIGS. 1C & 1G show top views of the third layer (layer 3) photomask in Designs 1 and 2, respectively. FIGS. 1D & 1H show top views of the overlap of the three layers (layers 1, 2, and 3) in Designs 1 and 2, respectively. Scale bar: 5 mm.

DETAILED DESCRIPTION OF THE INVENTION

Definitions

Figure 1A:
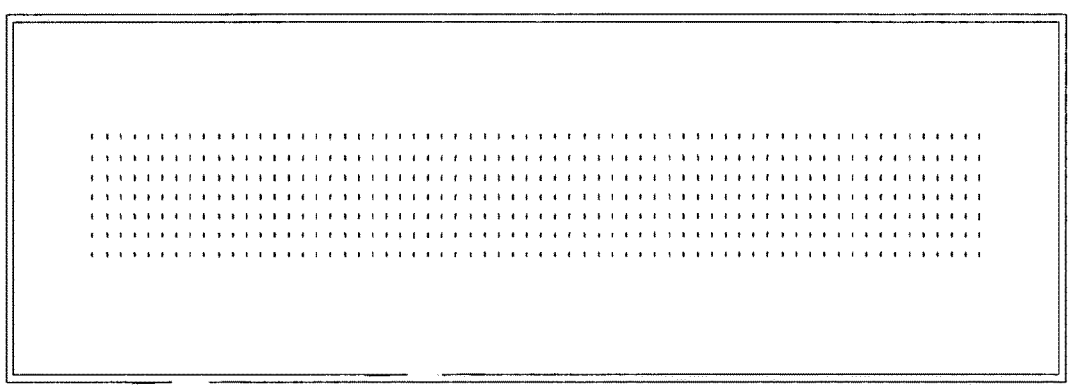
Figure 1B:
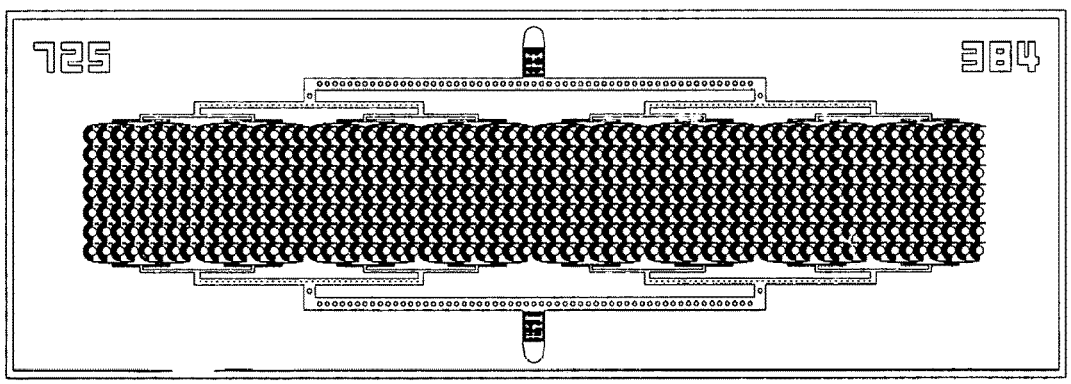
Figure 1C:
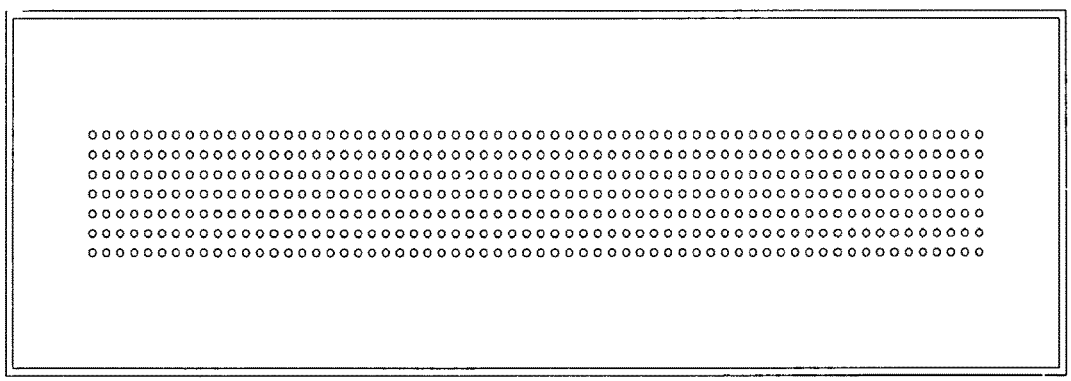
Figure 1D:
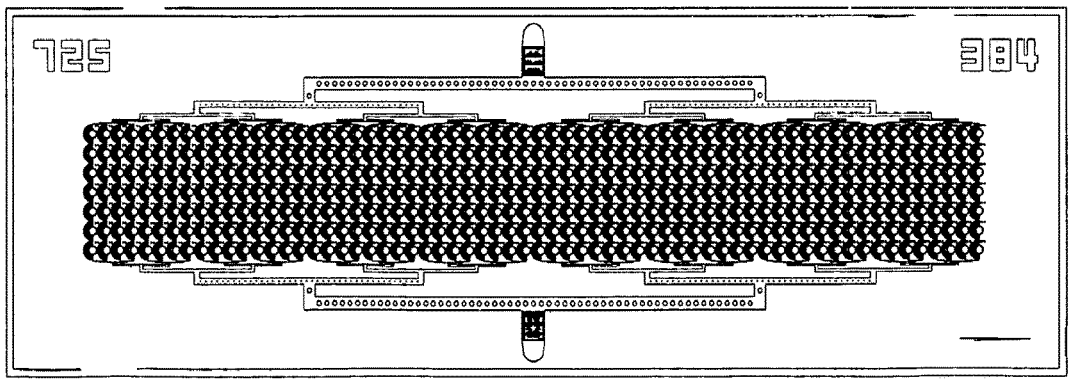

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, when a number or a range is recited, ordinary skill in the art understand it intends to encompass an appropriate, reasonable range for the particular field related to the invention.

By from 40 µm to 100 µm it meant that all integer unit amounts within the range are specifically disclosed as part of the invention. Thus, 40, 41, 42 . . . 97, 98, 99, and 100 µm unit amounts are included as embodiments of this invention.

By from 300 µm to 4000 µm it meant that all integer unit amounts within the range are specifically disclosed as part of the invention. Thus, 300, 301, 302 . . . 3997, 3998, 3999, and 4000 µm unit amounts are included as embodiments of this invention.

By from 500 µm to 2000 µm it meant that all integer unit amounts within the range are specifically disclosed as part of the invention. Thus, 500, 501, 502 . . . 1997, 1998, 1999, and 2000 µm unit amounts are included as embodiments of this invention.

As used herein, "a single-cell trapping unit" may be referred as "an unit".

As used herein, "chamber" shall generally mean a chamber with a spacious room for cell culture for more than 24 hrs, for cell spread, proliferation, and/or migration.

As used herein, "an inlet channel" shall generally mean a microchannel that connects the incoming channel of the first single-cell trapping unit in a column of an array to the inlet hole of a HSC device. Each column of an array has one inlet channel connected to the inlet of an HSC device. The inlet channels merge into one microchannel before they are connected to the inlet of an HSC device. The inlet channels between the columns are in fluidic connection.

As used herein, "an outlet channel" shall generally mean a microchannel that connects the outgoing channel of the last single-cell trapping unit in a column of an array to the outlet hole of a HSC device. Each column of an array has one outlet channel connected to the outlet of an HSC device. The outlet channels merge into one microchannel before they are connected to the outlet of an HSC device. The outlet channels between the columns are in fluidic connection.

The terms "one single cell" and "one isolated single cell" are interchangeable.

The term "two single cells" and "two isolated single cells" are interchangeable.

The term "thermoplastic materials" shall generally mean plastic materials or polymers that become pliable or moldable above a specific temperature and solidifies upon cooling.

Abbreviations: hydrodynamic shuttling chip (HSC).

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Methods

Device design and fabrication. The microfluidic HSC devices were fabricated with polydimethylsiloxane (PDMS) using soft lithography techniques as previously described. First, a 5 µm thick layer of negative photoresist (SU-8, MicroChem, Newton, Mass., USA) was spin-coated onto a silicon wafer and exposed to UV light under a mask with the 5 µm width trapping channel. Second, a 25 µm thick layer of negative photoresist was spin-coated onto the same silicon wafer and exposed to UV light under another mask with 25 µm width by-pass channel. Third, a 50 µm thick layer of negative photoresist was spin-coated onto the same silicon wafer and exposed to UV light under another mask with a 500 µm diameter chamber for Design 1 (FIGS. 1A-D), whereas for Design 2, a 50 µm thick layer of negative photoresist was spin-coated onto the same silicon wafer and exposed to UV light under another mask with a 2000 µm diameter chamber (FIGS. 1E-H). The masters were then used as molds, on which Sylgard 184 (Dow corning, USA) PDMS pre-polymer mixed with its cross-linker at 10:1 ratio was poured and allowed to cure in a conventional oven at 65° C. overnight. The cured PDMS replicas were peeled off from the molds. A puncher with 0.75 mm inner-diameter (HARRIS UNI-CORE™, Ted Pella, USA) was used to punch one inlet and one outlet holes to introduce fluid into the fluidic channel of the PDMS device. After a brief oxygen plasma treatment, both the replica of the PDMS and a glass slide were brought to contact and placed in an oven at 65° C. for 24 hours to achieve permanent bonding.

HSC device preparation for multiple single-cell capturing. Prior to cell experiments, HSC devices were filled with deionized water and soaked in a deionized water-filled container in a desiccator to remove air bubbles in the microchannel. Subsequently, the degased HSC devices were exposed to UV light to sterilize for 30 minutes. To prevent immediate cell adhesion to the PDMS surface, 5% BSA (Bovine serum albumin, Bersing Technology, Taiwan) in 1×PBS was injected into the microfluidic channel and incubated at 37° C. for 30 minutes.

Cell culture and maintenance. Human breast cancer MDA-MB-231 and MCF-7 cell lines were used as cell models in the study. MDA-MB-231 and MCF-7 cells were cultured in DMEM medium (Gibco, USA) with 10% fetal bovine serum (Hyclone Thermo, USA) and 1% antibiotics (Glutamine-Penicillin-Streptomycin, Biowest, France) at 37° C. and 5% $CO_2$ in a humidified incubator. The cell cultures were passaged using trypsin-EDTA (0.25% in PBS, Biowest, France) according to the manufacture's standard protocol at 70-80% confluence.

Multiple single-cell capture, separate and culture. Prior to each cell-capture experiment, the cells were pre-stained with 4 mM membrane dye DiIC12(3) (BD Biosciences, USA) or 4 mM membrane-permeable live-cell labeling dye calcein-AM (Invitrogen, Life Technologies, USA) for 30 minutes for easy-identification of cells in the HSC device. For each single-cell capture experiment in Design 1 HSC devices, 1 µL of MCF-7 cells at $1.0 \times 10^6$ cells/mL concentration (total of $1 \times 10^3$ cells) was loaded into the microfluidic channel at 10 µL/min flow rate by using a syringe pump (Harvard Apparatus, Harvard Bioscience, USA) and Teflon tubing (inner dia.: 0.51 mm, outer dia.: 0.82 mm, Ever Sharp Technology, Inc., Taiwan). Then, 5 µL DMEM medium was loaded into the microfluidic channel at 0.3 µL/min flow rate. Subsequently, a reversed flow of 0.6 µL DMEM at 10 µL/min flow rate was used to release and move the cells into the chambers. For Design 2 HSC devices, 1 µL of MDA-MB-231 or MCF-7 cells at $1.0 \times 10^5$ cells/mL concentration (total of $5 \times 10^2$ cells) was loaded into the microfluidic channel at 0.3 µL/min flow rate by using a syringe pump (Harvard Apparatus, Harvard Bioscience, USA) and Teflon tubing (inner dia.: 0.51 mm, outer dia.: 0.82 mm, Ever Sharp Technology, Inc., Taiwan). Then, 5 µl DMEM medium was loaded into the microfluidic channel at 0.3 µL/min flow rate. Subsequently, a reversed flow of 10 µL DMEM at 200 µL/min flow rate was used to release and move the cells into the chambers. The term "multiple-single-cell capture" means a HSC device allows for capturing one cell in a chamber at a time and by repeating the procedure multiple isolated, single cells can be captured in a chamber. "separate" means when the cells are each captured in a chamber, they are physically separated (although the microchannels are in fluidic connection with the chambers). This feature allows minimal disturbance to other cells while one single cell is being manipulated.

Cell imaging. All cell images were obtained using an inverted microscope (Nikon Ti-E inverted fluorescence microscope, Japan) with an attached charge-coupled device (Retiga-4000DC, Qimaging, Canada) and control software (NIS-Elements Ar, Nikon, Japan).

Results

Device design and operation. The microchannel device is made out of PDMS and bounded to a glass substrate. To make the PDMS part, a three-layer SU-8 master mold was microfabricated using photolithography. We have made two HSC designs. FIGS. 1A-1D show top views of the first layer photomask, the second layer photomask, the third layer photomask, and the overlap of the three layers of photomasks, respectively, in Design 1. FIGS. 1E-1H show top views of the first layer photomask, the second layer photomask, the third layer photomask, and the overlap of the three layers of photomasks, respectively, in Design 2.

Figure 2:
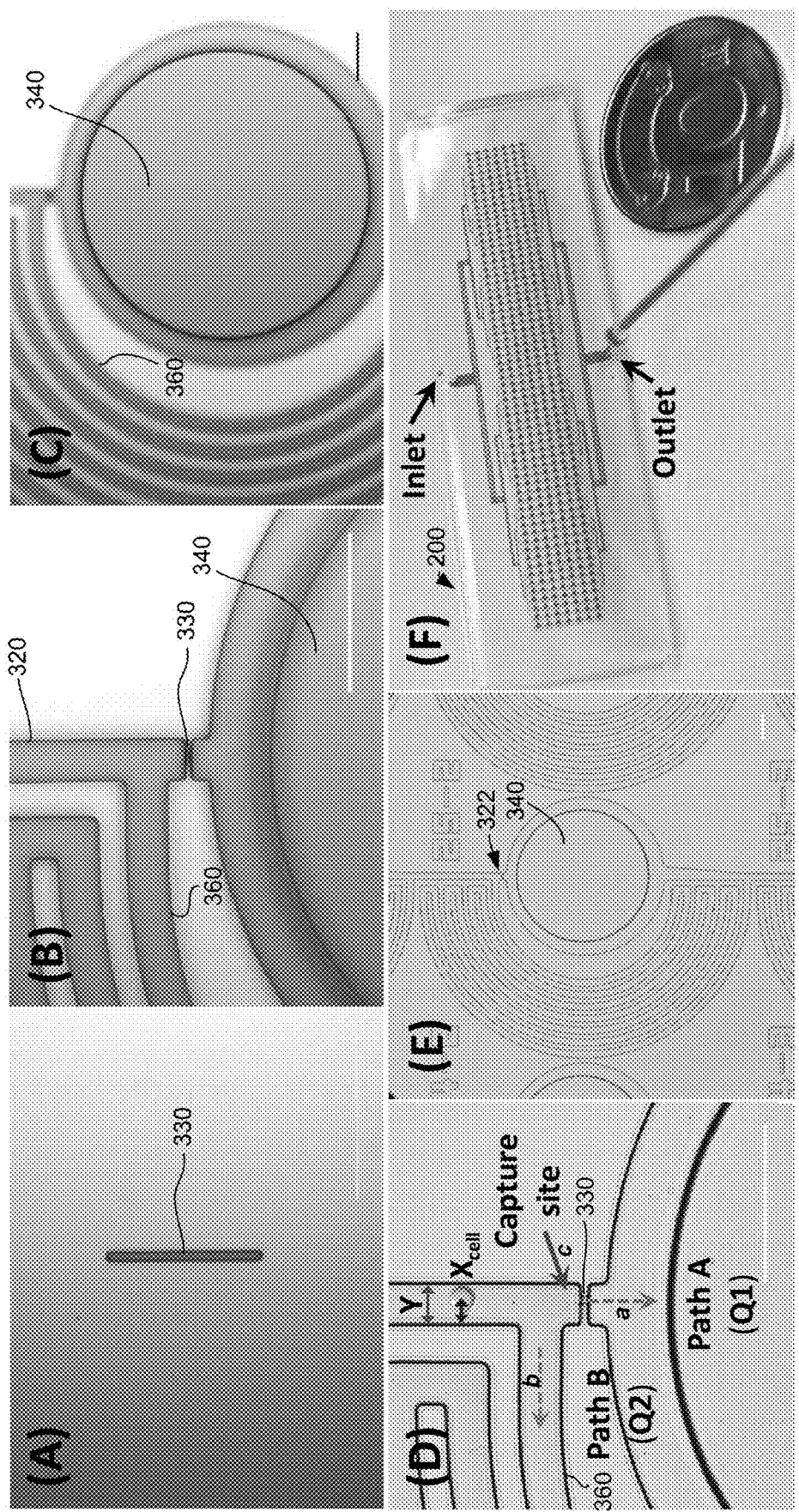
FIG. 2 shows top view photographs of SU-8 mold (A-C) and PDMS-on glass device of a hydrodynamic shuttling chip (HSC) device (D-F) in Design 1. (A) A photograph of a trapping channel (layer 1) with 3.8 µm length, 5.0 µm width and 4.3 µm height. (B) A photograph showing a by-pass channel (layers 1, 2, and 3 overlapped) with 25.0 µm width and 23.0 µm height. (C) A photograph showing a chamber with 500.6 µm diameter and 57.8 µm height (depth). (D) a microscope image showing hydrodynamic structures (arrowheads a and b indicate different flow resistance; arrowhead c indicates a cell capture site). (E) A magnified view showing a single-cell trapping unit. (F) A photograph showing the appearance of a HSC device made with PDMS. The volumetric flow rate is defined as Q. The volumetric flow rate in path A is indicates as Q1 and the volumetric flow rate in path B is indicated as Q2. Scale bar: 100 µm.
Figure 3:
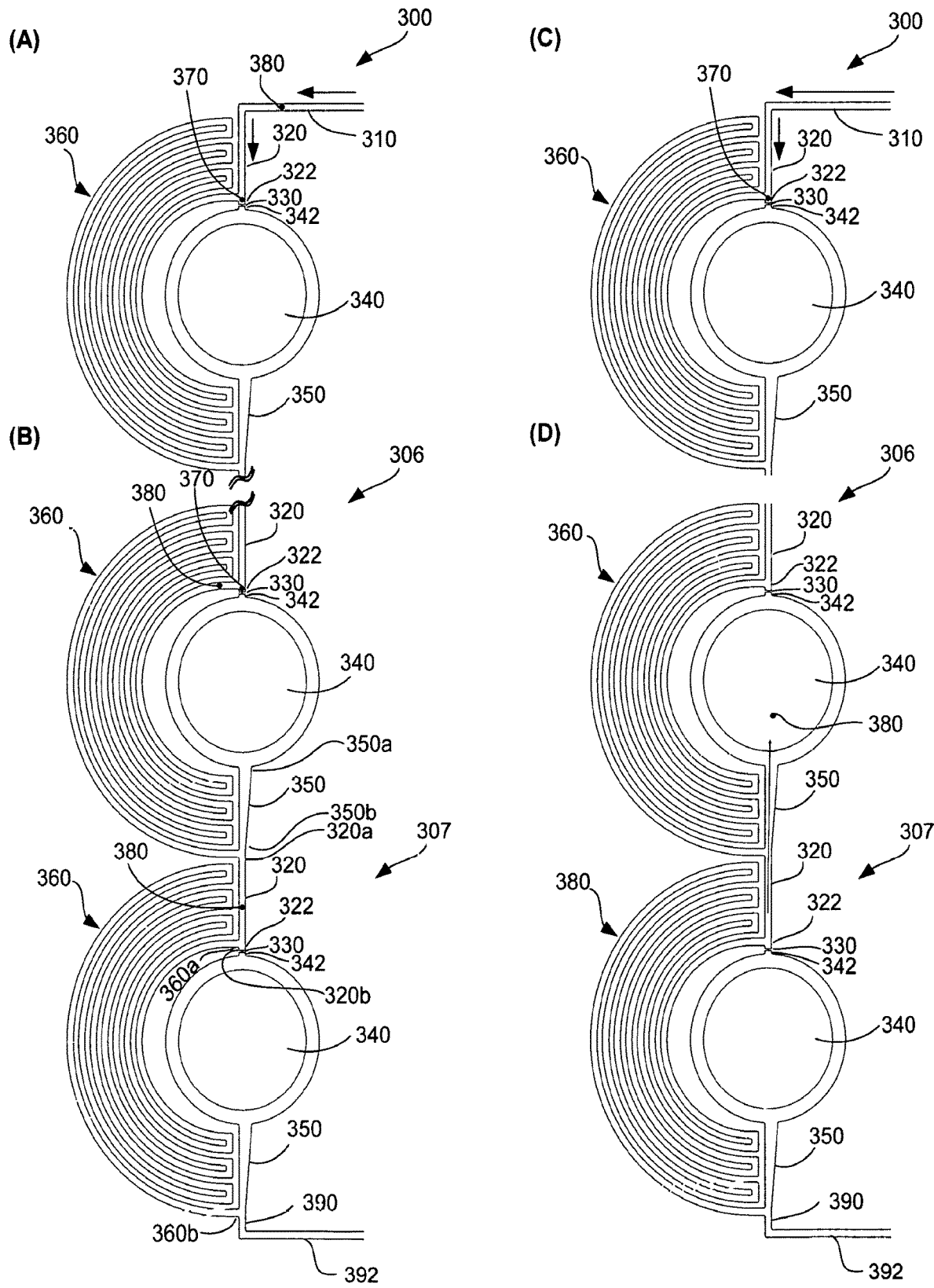
FIG. 3 is a schematic drawing showing HSC device operation procedure. (A) a cell loading step showing flow direction. (B) When a cell is trapped at the trapping site, which causes an increase in the flow resistance of the fluid path to the chamber, the following cell will flow toward the serpentine by-pass channel. (C) A cell culture medium is used to wash excess cells in microchannel. (D) The captured cell is released from the trapping site and flowed into a chamber.

FIG. 2 shows top view of the pictures of the SU-8 mold (A-C) and finished PDMS-on glass HSC device (D-F) of the Design 1. FIG. 2A shows the first layer with a trapping channel 330 in (each is 3.8 µm in length, 5.0 µm in width and 4.3 µm in height) of the SU-8 structure. The second layer creates by-pass channels 360 (each is 25.0 µm in width and 23.0 µm in height) and chambers 340 (each is 500 µm in diameter and 23.0 µm in height) which are connected to the by-pass channels 360 via the trapping channels 330 (FIG. 2B). The third layer (57.8 in height) was built on the top of the second layer to create and increase the chambers' height and their volumes (FIG. 2C). Thus, the final height of the chamber in Design 1 device is 57.8 µm. For Design 2, each of the trapping channels is 5.1 µm long, 6.5 µm wide and 4.9 µm high. The by-pass channels are 25 µm wide and 23.3 high whereas each of the chambers is 2500 µm in diameter and 82.0 µm high.

Referring to FIG. 2D, to ensure each cell capture site only traps one single cell, the volumetric flow rates of Q1 and Q2 (Q1 and Q2 are the volumetric flow rates going through the path A and path B, respectively) are designed in a way that the first incoming cell will go through path A (i.e., moving toward trapping channel 330; the direction marked by arrowhead a) instead of path B (i.e., moving toward by-pass channel 360; the direction marked by arrowhead b), resulting in the cell being trapped at the capture site (marked by arrowhead c). After trapping a cell at the capture site, the flow resistance of the path A is increased, so that the ratio of Q1 to Q2 is decreased resulting in the next incoming cell going through path B instead of path A. The Darcy-Weisbach equation can be used to calculate the resistance of microchannels (Eqn. 1):

$$\Delta P = \frac{C(\alpha)}{32} \frac{\mu L Q R^2}{A^3} \quad \text{(Eqn. 1)}$$

where P is the driving pressure of the fluid, $C(\alpha)$ is a constant of the aspect ratio ($0 < \alpha < 1$) of the microchannel, µ is the fluidic viscosity, L is the length of channel, Q is the volumetric flow rate, R is the perimeter and A is the cross-sectional area of microchannels, respectively.

In order to ensure the designed trapping channel 330 will work at any flow velocity in a laminar flow system, the center of cells must be situated inside of the path A stream line. We define the distance of the cell's center to the incoming channel wall as X and the incoming channel width is Y. When $Q_1/Q_2$ ratio is greater than the value of $(Y-X)/X$, the cells will be trapped at the capture site at any flow velocity in laminar flow region (Eqn. 2).

$$\frac{Q_1}{Q_2} > \left(\frac{Y-X}{X}\right) \quad \text{(Eqn. 2)}$$

For Design 1 HSC, the fabricated device has a Q1/Q2 value of 3.563, which is greater than the threshold value of 2.125 (Table 1), ensuring that the first incoming cell goes through path A instead of path B and being trapped at the capture site. FIG. 2E shows a magnified view of a capture site 322 and a chamber 340 in a HSC device, whereas FIG. 2F shows the whole HSC device 200 containing 384 chambers and one inlet and one outlet holes. The Design 2 HSC device's Q1/Q2 value of 3.391 is also greater than its threshold value of 2.125 (Table 1). Table 1 shows microchannel resistance ratio.

TABLE 1

|  | Layer 1 width | Layer 1 height | Layer 2 width | Layer 2 height | Layer 3 width | Layer 3 height | Q1/Q2 |
|---|---|---|---|---|---|---|---|
| Design 1 minimum | 5.0 µm | 5.0 µm | 25.0 µm | 25.0 µm | 500.0 µm | 50.0 µm | 2.125 |
| Results | 5.0 µm | 4.3 µm | 25.0 µm | 23.0 µm | 500.6 µm | 57.8 µm | 3.563 |
| Design 2 minimum | 6.0 µm | 5.0 µm | 25.0 µm | 25.0 µm | 2000.0 µm | 50.0 µm | 2.125 |
| Results | 6.5 µm | 4.9 µm | 25.0 µm | 23.3 µm | 2000.0 µm | 82.0 µm | 3.391 |

The applicable cell size for HSC is dependent on the dimensions of the trapping channel and by-pass channel. The cell size need to be smaller than the cross section of the by-pass channel to avoid cell from clogging by-pass channel, and at the same time larger than the cross section of the trapping channel to prevent the cell from going through the trapping channel without being trapped at the capture site.

Referring to FIG. 2D-F and FIG. 3, HSC device 200 comprises an array of single-cell trapping units, in which each of the single-cell trapping units comprises: (a) an incoming channel 320 with length L1, width W1, and height H1, having an anterior end 320a and a posterior end 320b opposite to the anterior end, wherein the posterior end has a capture site 322; (b) a chamber 340 with diameter M and depth D, located posterior to the capture site 322 of the incoming channel 320 and having a receiving site 342 spaced apart from the capture site 322 at a distance of g, the chamber 340 having an interior space adapted for more than one single cell to attach, grow, proliferate, and/or migrate; (c) a trapping channel 330 with length L2, width W2, height H2, located between the capture site 322 and the receiving site 342 and being in fluid connection with the incoming channel 320 and the chamber 340; (d) a chamber channel 350 with length L3, width W3, height H3, located posterior to and in fluidic connection with the chamber 340 and having an anterior end 350a and a posterior end 350b opposite to the anterior end 350a, the height H3 of the chamber channel 350 being smaller than the depth D of the chamber 340; and (e) a by-pass channel 360 with length L4, width W4, and height H4, located lateral to the incoming channel 320, chamber 340 and chamber channel 350 and having a first end 360a and a second end 360b opposite to the first end 360a, the first end 360a branching out from the incoming channel 320 immediately prior to the capture site 322 and the second end 360b joining the chamber channel at the posterior end 350b thereof, the width W4 and height H4 of the by-pass channel 360 being greater than the width W2 and height H2 of the trapping channel.

The operation procedure of the HSC device involves the following steps:

Referring to FIG. 3A, a cell suspension is loaded into inlet channel 310 of unit 300. Individual cells enters incoming channel 320 of the first unit 300 in a column of an array. The first single cell 370 is trapped at capture site 322 of incoming channel 320 of the first unit 300. The units 300, . . . , 306, 307 in a column of an array are in fluidic connection. The last unit 307 in each column of the array has an outgoing channel 390 connected to an outlet channel 392. Referring to FIG. 3B, when an individual cell 370 is trapped at capture site 322 of incoming channel 320 of unit 306, which results in an increase in the flow resistance of the fluid path to chamber 340, the following cell 380 will flow toward serpentine by-pass channel 360 of unit 306, then enters into incoming channel 320 of an immediately adjacent downstream unit 307, and trapped at capture site 322 thereof.

Referring to FIG. 3C, a cell culture medium is used to wash excess cells in microchannel. Referring to FIG. 3D, a culture medium is used to reflux microchannel through outlet channel 392 and outgoing channel 390 of unit 307. The captured cell 380 in unit 307 is released from capture site 322 of incoming channel 320 of unit 307, and then flowed into chamber 340 of an immediately adjacent upstream unit 306 through chamber channel 350 of unit 306.

For Design 1, 1) One µL of cell suspension is loaded into inlet channel at 10 µL/min flow rate by using a syringe pump. The individual single cells flow into the incoming channel of the first unit of a single column, and the first cell is trapped at the capture site (FIG. 3A). When a cell is trapped at the trapping site, which results in an increase in the flow resistance of the fluid path to the chamber, the following cell will flow toward the serpentine by-pass channel (FIG. 3B) and enters into the incoming channel of an immediate downstream unit (FIG. 3B). 2) Five microliters of fresh medium are loaded into the channel at 0.3 µL/min flow rate by using a syringe pump (FIG. 3C) to wash excess cells away from the microchannel. 3) Finally, a reversed flow of 0.6 µL fresh medium at 10 µL/min was introduced into microchannel to release the captured cells from the capture sites and transport these cells into the chambers. (FIG. 3D). Because the flow resistance into the chamber is less than through the by-pass channel, the released cells flow into the chamber, not the by-pass channel. In addition, because of the enlarged cross-section area of the chamber, the flow velocity is greatly reduced inside the chamber, which prevents the loaded cells in the chamber from being carried away by the flow and trapped at the junction of the receiving site and the trapping channel. For the demonstration of MCF-7 cells, the whole procedure can be performed in 20 min. By repeating the above steps individual cells of another cell type can be loaded into chambers.

For Design 2, the three operation steps are as follows: 1) Five microliters of cell suspension are loaded into the channel at 0.3 µL/min flow rate by using a syringe pump. In this step the individual single cells are trapped in the capture sites. 2) Five microliters of fresh medium is loaded into the channel at 0.3 µL/min flow rate by using a syringe pump to wash excess cells from the microchannel. 3) Finally, a reversed flow at 200 µL/min of 10 µL fresh medium is introduced into the microchannel to release the captured cells from the capture sites and transport these cells into the chambers. The entire procedure can be performed in 40 min.

Figure 4:
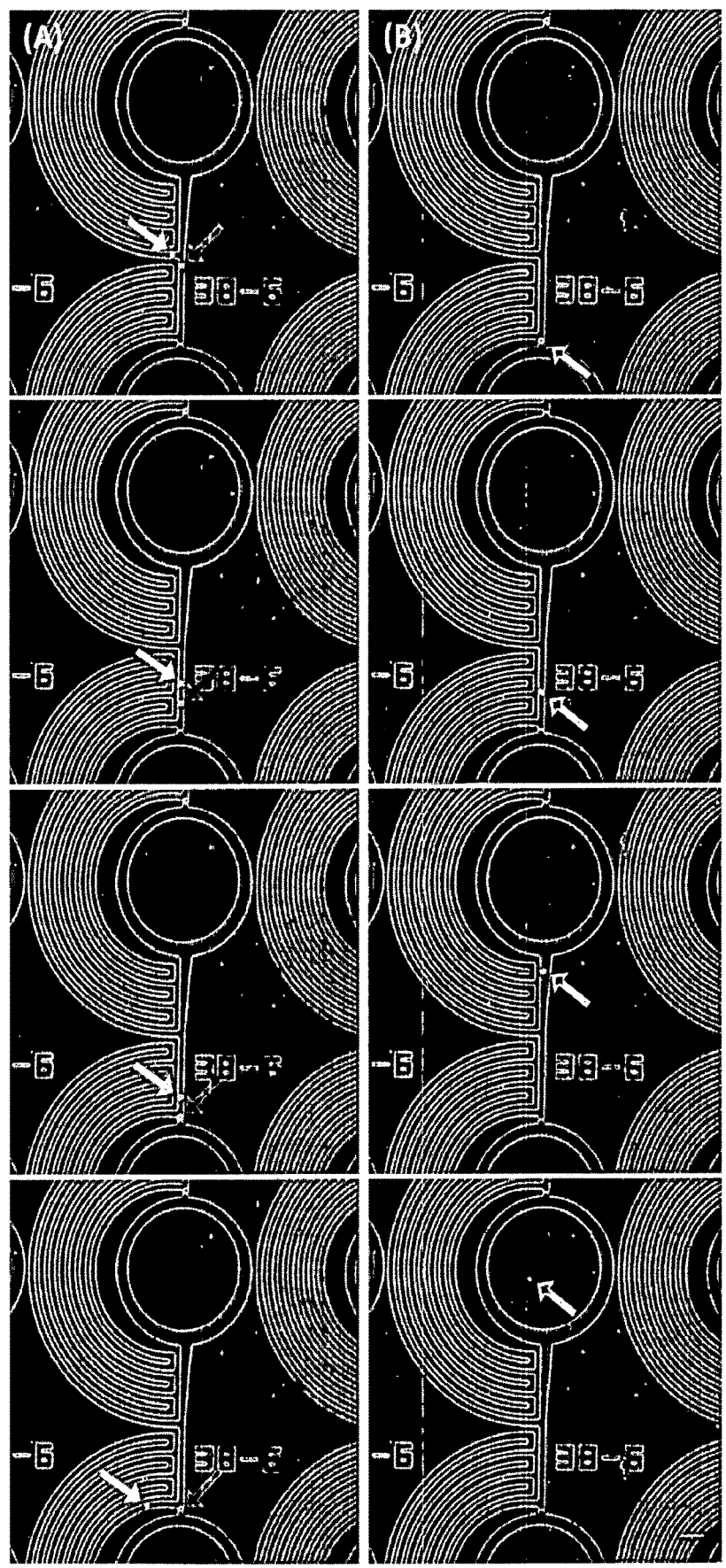
FIG. 4 shows sequential images of MCF-7 single-cell capture in a chamber. Column (A), top image showing two single cells from the by-pass channel of an upstream unit entering the incoming channel of a downstream unit; the second image showing the two single cells flowing toward the capture site of the downstream unit; the third image showing the cell at the front (the first cell) is trapped at the capture site of the incoming channel of the downstream unit; the bottom image showing the following single cell (the second cell) by-passing the capture site. Column (B), top image showing the first cell trapped at the capture site; the second image showing the first cell being released from the capture site; the third image showing the first cell flowing in the chamber channel; the bottom image showing the first cell entering the chamber. Scale bar: 100 µm.

FIG. 4 shows sequential images of MCF-7 single-cell capture in a chamber. Referring to column (A): The top image shows two single cells near the intersection between the by-pass channel and incoming channel, in which the first cell is in the incoming channel of a downstream unit, and the second cell in the by-pass channel of an upstream unit. The second image shows the first cell flowing toward the chamber capture site of the downstream unit, and the second cell having flowed into the incoming channel of the downstream unit. The third image shows the first cell being trapped at the capture site of the downstream unit, and the second cell following behind the first cell. The bottom image shows the second cell by-passing the capture site and flowing into the by-pass channel of the downstream unit.

Referring to column (B) of FIG. 4: The top image shows a individual cell (the first cell) trapped at the capture site of a downstream unit. The second image shows the first cell being released from the capture site of the downstream unit. The third image shows the first cell in the chamber channel flowing toward the chamber of an immediately adjacent upstream unit. The bottom image shows the first cell in the chamber of the immediately adjacent upstream unit.

Figure 5:
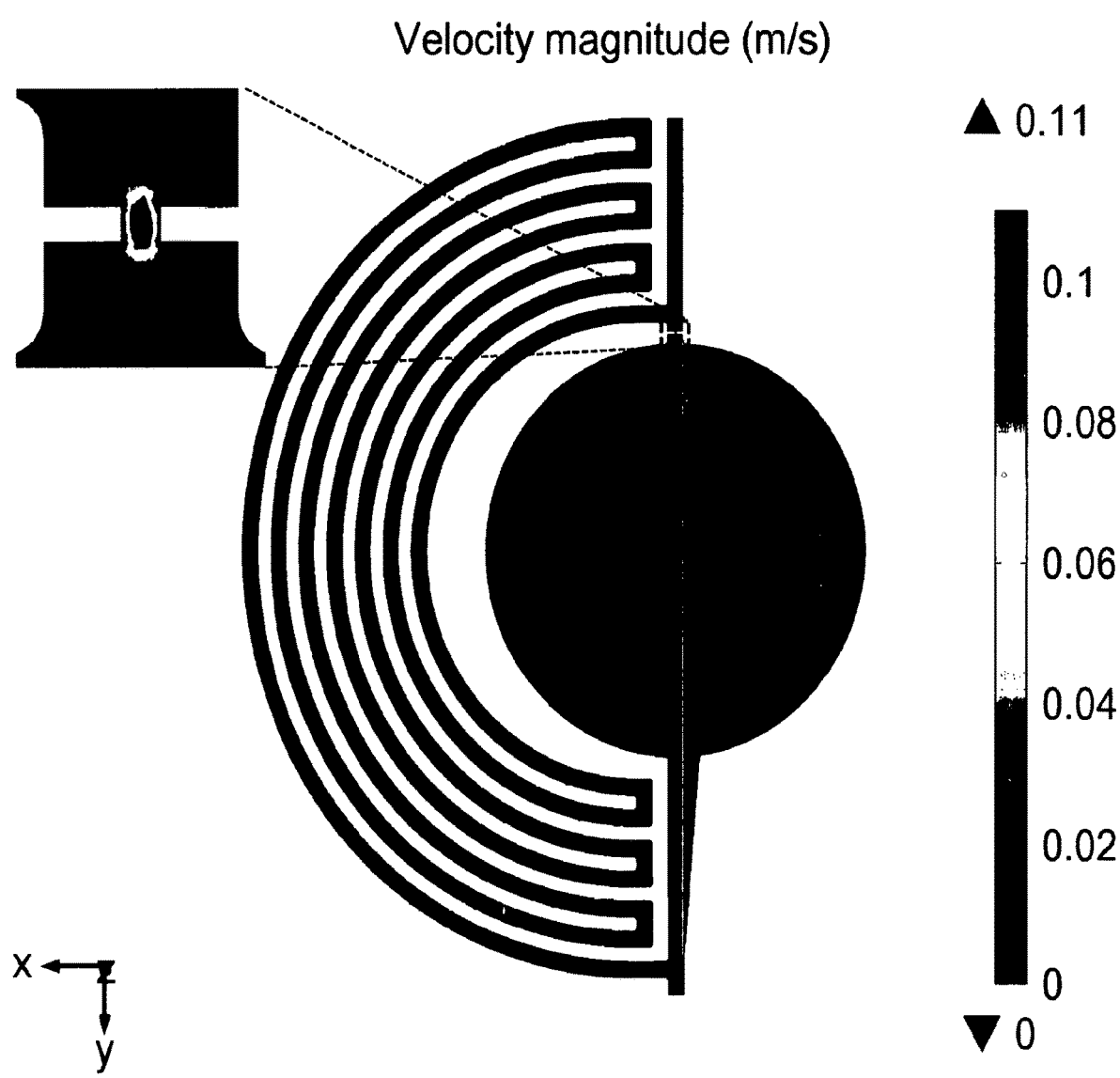
FIG. 5 shows flow velocity simulation by COMSOL. Results of flow velocity field and streamlines. Flow velocity at the trapping channel is higher than that in the by-pass channel and chamber.

COMSOL simulation. The laminar flow module of COMSOL was used to simulate flow velocity under the operation procedure. The flow velocity through the trapping channel is much higher than that of the by-pass channel, indicating that the injected cells will flow toward the trapping channel (FIG. 5). The simulation result also shows that the large cross section area of the chamber greatly reduced the streamline flow velocity in the chamber.

Figure 6:
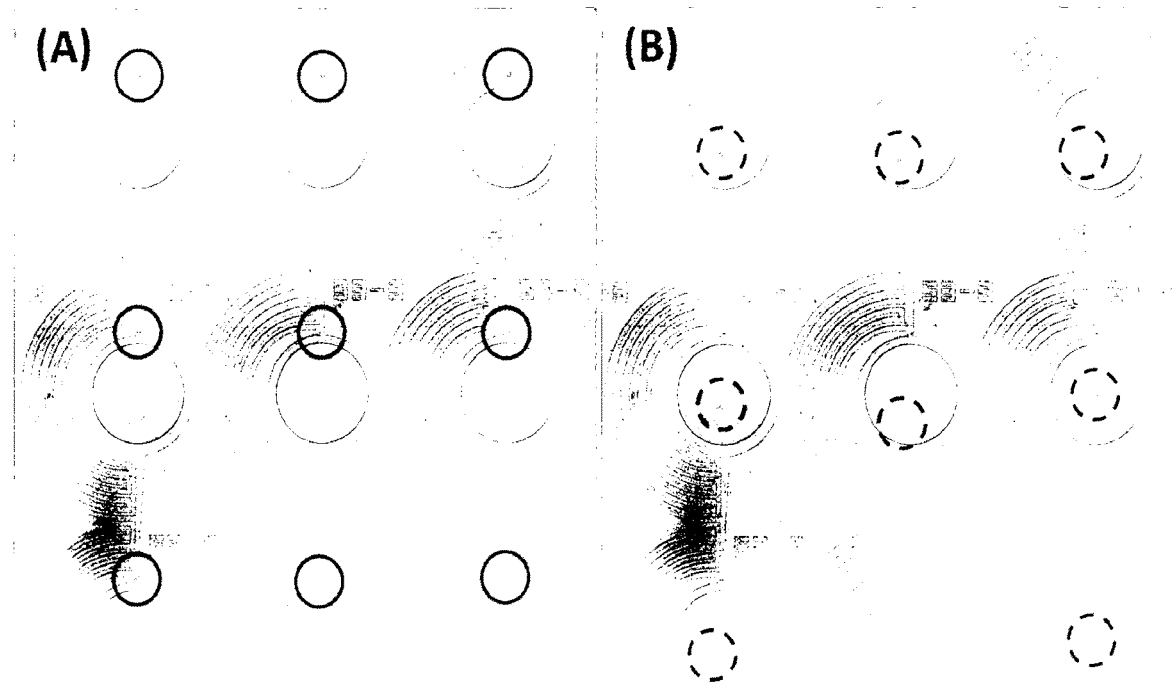
FIG. 6 shows the MCF-7 cell capture efficiency in Design 1 HSC device. (A) A photograph of captured single cells (marked with solid line circles) at the capture sites. (B) a photograph of captured single cells (marked with dash line circles) in the chambers. (C) Efficiencies of single cell trapping at the capture sites and single cell capture in the chambers. Cells were stained with green calcein-AM fluorescent dye. Scale bar: 100 µm.
Figure 6:
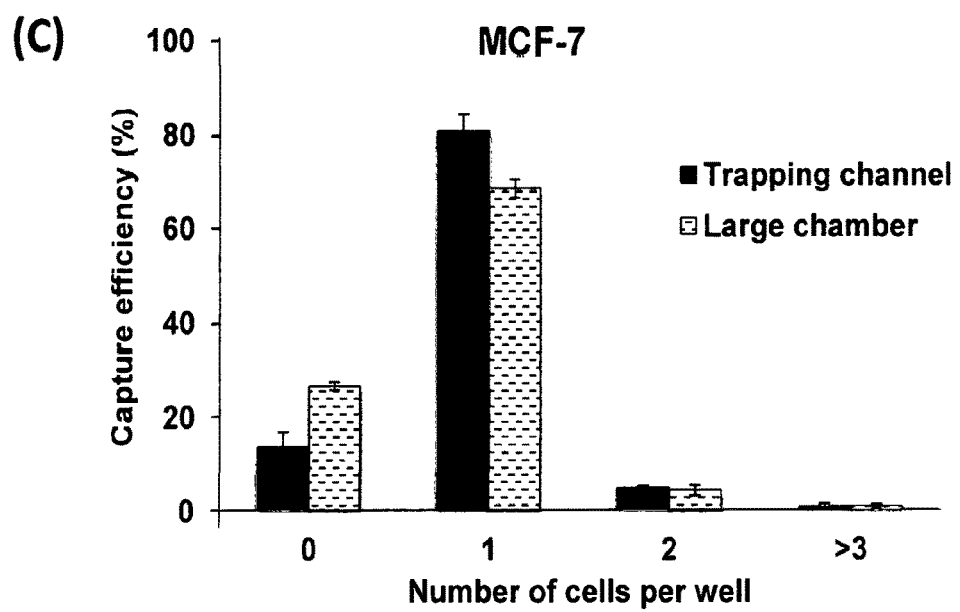

FIG. 6 shows the MCF-7 cell capture efficiency in HSC Design 1 device. Cells were stained with green Calcein-AM fluorescent dye for observations. FIG. 6A shows single cells captured at the capture sites (marked with solid line circles), and FIG. 6B shows the captured single cells in the chambers (marked with dash line circles). FIG. 6C shows efficiencies of single cell trapping at the capture sites and single cell capture in the chambers.

Figure 7:
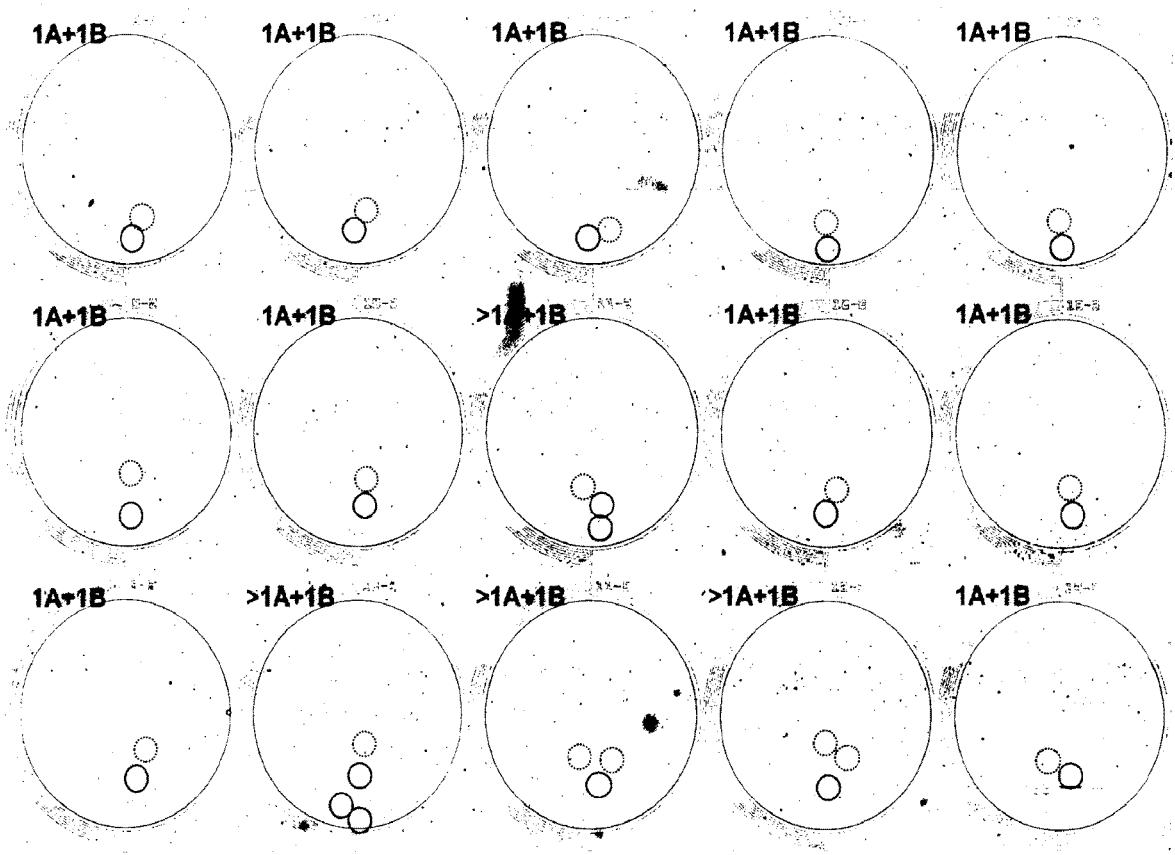
FIG. 7 is a photograph showing the pairing results of MDA-MB-231 and MCF-7 single cells in chambers of a Design 2 HSC device. MCF-7 cells were stained with green Calcein-AM fluorescent dye (marked with solid line circles) and MDA-MB-231 cells were stained with red DiI fluorescent dye (marked with dash line circles. The term "1A+1B" denotes "one single MDA-MB-231 cell and one single MCF-7 cell". The term ">1A+1B" denotes "more than one single MDA-MB-231 cell and one single MCF-7 cell". Scale bar: 1 mm.

FIG. 7 shows the pairing results of MDA-MB-231 and MCF-7 single cells in Design 2 HSC device. Top view photograph of paired single cells in the chambers. MCF-7 cells (marked with solid line circles) were stained with green Calcein-AM fluorescent dye and MDA-MB-231 cells (marked with dash line circles) were stained with red DiI fluorescent dye. Scale bar: 1 mm. The term "1A" denotes "one single MDA-MB-231 cell". The term "1B" denotes "one single MCF-7 cell". The term "1A+1B" denotes "one single MDA-MB-231 cell and one single MCF-7 cell", The term ">1A+1B" denotes "more than one single MDA-MB-231 cell and one single MC-F-7 cell", i.e., one single MCF-7 and one single MDA-MB-231 cells, plus additional more than one single MCF-7 or MDA-MB-231 cell.

Figure 8:
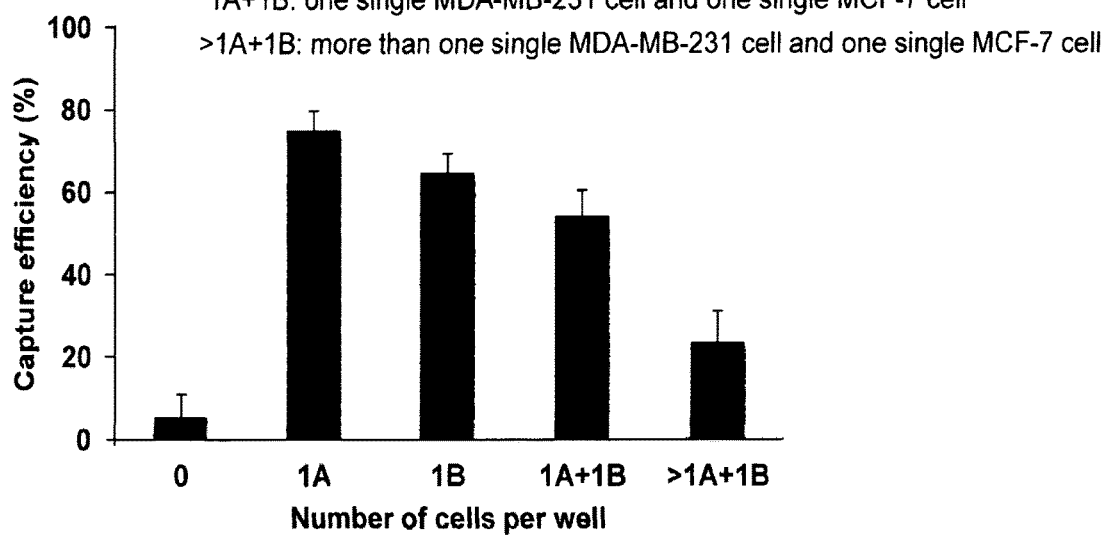
FIG. 8 shows capture efficiencies of single and multiple single cells in chambers. The term "1A" denotes "one single MDA-MB-231 cell". The term "1B" denotes "one single MCF-7 cell". The term "1A+1B" denotes "one single MDA-MB-231 cell and one single MCF-7 cell". The term ">1A+1B" denotes "more than one single MDA-MB-231 cell and one single MCF-7 cell".

FIG. 8 shows capture efficiencies of single and multiple single cells in the chambers shown in FIG. 7.

The foregoing description of the exemplary embodiments of the invention has been presented only for the purposes of illustration and description and is not intended to be exhaustive or to limit the invention to the precise forms disclosed. Many modifications and variations are possible in light of the above teaching. The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A hydrodynamic shuttling chip device comprising an array of single-cell trapping units, each of the single-cell trapping units comprising:

(a) an incoming channel with length L1, width W1, and height H1, having an anterior end and a posterior end opposite to the anterior end, wherein the posterior end has a cell capture site for trapping at least one single cell;

(b) a cell culture chamber with diameter M and depth D, located posterior to the cell capture site of the incoming channel and having a receiving site spaced apart from the capture site at a distance of g, the chamber having an interior space adapted for more than one single cell to attach, grow, proliferate, and/or migrate, and whereby the cell culture chamber is sized to enable cell spread, proliferation, and/or migration for more than 24 hours;

(c) a trapping channel with length L2, width W2, height H2, located between the capture site and the receiving site and being in fluid connection with the incoming channel and the cell culture chamber;

(d) a chamber channel with length L3, width W3, height H3, located posterior to and in fluidic connection with the cell culture chamber and having an anterior end and a posterior end opposite to the anterior end, the height H3 of the chamber channel being smaller than the depth D of the cell culture chamber; and (e) a by-pass channel with length L4, width W4, and height H4, located lateral to the incoming channel, the cell culture chamber and the chamber channel and having a first end and a second end opposite to the first end, the first end branching out from the incoming channel immediately prior to the capture site and the second end joining the chamber channel at the posterior end thereof, the width W4 and height H4 of the by-pass channel being greater than the width W2 and height H2 of the trapping channel; such that after a first cell is trapped in the trapping channel, a flow resistance of a path through the trapping channel is created causing a second cell, in the incoming channel, to move on a path through the by-pass channel;

wherein in each column of the array:
(i) the single-cell trapping units are in fluidic connection;
(ii) the incoming channel of each unit, except the first unit, is in fluid connection with the chamber channel of an immediately upstream unit; and
(iii) the by-pass channel of each unit, except the last unit, is in fluid connection with the incoming channel of an immediately downstream unit.

2. The hydrodynamic shuttling chip device of claim 1, wherein in each column of the array the chamber channel of each unit except the last unit is in fluidic connection with the incoming channel of an immediately adjacent downstream unit.

3. The hydrodynamic shuttling chip device of claim 2, wherein in each column of the array the chamber channel of the last unit is in fluid connection with an outgoing channel.

4. The hydrodynamic shuttling chip device of claim 3, wherein in each column of the array the incoming channel of the first unit is in fluidic connection with an inlet channel, and the outgoing channel of the last unit is in fluidic connection with an outlet channel.

5. The hydrodynamic shuttling chip device of claim 4, further comprising:
(a) an inlet port, being in fluid connection with the inlet channel; and
(b) an outlet port, being in fluid connection with the outlet channel.

6. The hydrodynamic shuttling chip device of claim 1, wherein the single-cell trapping units between columns of the array are in fluidic connection via the inlet channel and the outlet channel.

7. The hydrodynamic shuttling chip device of claim 1, wherein the surfaces of the incoming channel, trapping channel, chamber channel, and by-pass channel are coated with albumin.

8. The hydrodynamic shuttling chip device of claim 1, further comprising one or more types of isolated single cells in the cell culture chamber.

9. The hydrodynamic shuttling chip device of claim 8, wherein the device comprises at least two types of isolated single cells in the cell culture chamber.

10. The hydrodynamic shuttling chip device of claim 1, further comprising a single cell suspension, wherein the size of a single in the suspension is smaller than the cross section of the by-pass channel but larger than the cross section of the trapping channel.

11. The hydrodynamic shuttling chip device of claim 1, wherein the device is bonded onto a transparent substrate.

12. The hydrodynamic shuttling chip device of claim 1, wherein the device is made of a material selected from the group consisting of polydimethylsiloxane, polymethyl methacrylate, and polycarbonate, glass, thermoplastic materials, and any combination thereof.

13. The hydrodynamic shuttling chip device of claim 1, wherein the by-pass channel serpentines laterally through one side of the unit.

14. A method of capturing isolated single cells, comprising:
(a) providing a hydrodynamic shuttling chip device as claimed in claim 7;
(b) loading culture medium comprising isolated cells of a single type into the incoming channel of the first single-cell trapping unit in a single row of the array;
(c) capturing the isolated single cell at the capture site;
(d) washing away uncaptured, excess cells with a fresh culture medium; and
(e) refluxing the channels with a medium to release the captured isolated cell and reversely flow the released cell into the cell culture chamber.

15. A method of capturing isolated single cells of more than one type, comprising:
(a) providing a hydrodynamic shuttling chip device as claimed in claim 7;
(b) loading culture medium comprising isolated single cells of a specific type into the incoming channel of the first single-cell trapping unit in a single row of the array;
(c) capturing the isolated single cell at the capture site;
(d) washing away uncaptured, excess cells with fresh culture medium; and
(e) refluxing the chamber channels to release the captured cell and reversely flow the released cell into the cell culture chamber; and
(f) repeating the loading, capturing, washing, and refluxing steps one or more times with the proviso that in each repeating step the isolated single cells are a different type.

* * * * *